United States Patent [19]

Verhoeven et al.

[11] Patent Number: 5,679,659

[45] Date of Patent: Oct. 21, 1997

[54] METHOD FOR MAKING HEPARINIZED BIOMATERIALS

[75] Inventors: Michel Verhoeven, Maastricht; Linda L. Cahalan, Geleen; Marc Hendriks; Benedicte Fouache, both of Hoensbroek; Patrick T. Cahalan, Geleen, all of Netherlands

[73] Assignee: Medtronic, Inc., Minneapolis, Minn.

[21] Appl. No.: 518,084

[22] Filed: Aug. 22, 1995

[51] Int. Cl.$^6$ .......................... A61K 31/725; C08B 37/10
[52] U.S. Cl. ................. 514/56; 536/21; 536/124; 623/1; 623/11; 604/266; 606/76
[58] Field of Search .................. 536/21, 124; 623/1, 623/11; 604/266; 606/76; 514/56

[56] References Cited

U.S. PATENT DOCUMENTS

| | | | |
|---|---|---|---|
| 4,118,485 | 10/1978 | Eriksson et al. | 514/56 |
| 4,521,564 | 6/1985 | Solomon et al. | 525/54.1 |
| 4,526,714 | 7/1985 | Feijen et al. | 530/363 |
| 4,565,740 | 1/1986 | Golander et al. | 428/409 |
| 4,600,652 | 7/1986 | Solomon et al. | 424/423 |
| 4,613,665 | 9/1986 | Larm | 536/20 |
| 4,634,762 | 1/1987 | Feijen et al. | 530/350 |
| 4,642,242 | 2/1987 | Solomon et al. | 427/2.12 |
| 4,673,584 | 6/1987 | Nygret et al. | 427/2.1 |
| 4,720,512 | 1/1988 | Hu et al. | 523/112 |
| 4,786,556 | 11/1988 | Hu et al. | 428/412 |
| 5,032,666 | 7/1991 | Hu et al. | 528/70 |
| 5,049,403 | 9/1991 | Larm et al. | 427/2.1 |
| 5,077,372 | 12/1991 | Hu et al. | 602/48 |
| 5,116,962 | 5/1992 | Stuber et al. | 525/54.2 |
| 5,132,108 | 7/1992 | Narayanan et al. | 424/78.17 |
| 5,229,172 | 7/1993 | Cahalan et al. | 427/536 |
| 5,308,641 | 5/1994 | Cahalan et al. | 427/2.1 |
| 5,350,800 | 9/1994 | Verhoeven et al. | 525/54.2 |
| 5,356,433 | 10/1994 | Rowland et al. | 623/11 |
| 5,415,938 | 5/1995 | Cahalan et al. | 428/409 |
| 5,476,509 | 12/1995 | Keogh et al. | 623/1 |

FOREIGN PATENT DOCUMENTS

| | | |
|---|---|---|
| 0203463B1 | 6/1991 | Germany. |
| 1319007 | 5/1973 | United Kingdom. |

OTHER PUBLICATIONS

Lars–Ake Fransson et al, "Periodate Oxidation and Alkaline Degradation of Heparin–Related Glycans", *Carbohydrate Research*, 80 (1980) 131–145, c Elsevier Scientific Pub. Co., Amsterdam, months not available.

H.E. Conrad et al, "Heparin and Related Polysaccharides", *In Advances in Experimental Medicine and Biology*, D.A. Lane et al., editors; vol. 313, pp. 31–36, 1992.

B. Casu, et al, "Retention of Antilipemic Activity by Periodate–Oxidized Non-Anticoagulant Heparins", *Arzneimittel Forschung Drug Research*, Apr. 1986.

*Primary Examiner*—Kathleen K. Fonda
*Attorney, Agent, or Firm*—Daniel W. Latham; Harold R. Patton

[57] ABSTRACT

An improved method of making a medical device having immobilized heparin on a blood-contacting surface in which heparin is admixed with sufficient periodate to react with not more than two sugar units per heparin molecule in a buffer solution having a pH in the range of about 4.5–8. This mixture is reacted for at least 3 hours while protected from light and is then applied to the immobilized amine groups. This is an improvement over the prior art methods which included using an excess of periodate and then stopping the reaction at a desired point by the addition of glycerol since the conversion of only a few of the natural functional groups to aldehydes better preserves the antithrombotic bioeffectiveness of the heparin molecules bound to the surface. The invention also avoids the prior art steps of drying and reconstituting the heparin by providing a reacted mixture of heparin and periodate that can be stored as a stable liquid and applied directly to the aminated surface several days later.

10 Claims, No Drawings

METHOD FOR MAKING HEPARINIZED BIOMATERIALS

BACKGROUND OF THE INVENTION

This invention relates to the enhancement of the biocompatibility of various surfaces by binding biomolecules which contain polysaccharide groups to animated surfaces and particularly to providing improved hemocompatability for biomaterials by covalent attachment of heparin.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" such as growth factors, antimicrobial agents, antithrombogenic agents, and cell attachment proteins to the surface of the material.

Immobilization of polysaccharides such as heparin to biomaterials has been researched extensively to improve bio- and hemocompatibility. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, covalent mobilization of heparin to a biomaterial consists of activating the material in such a way that coupling between the biomaterial and functional groups on the heparin (—COOH, —OH, —NH$_2$) can be achieved. Thromboresistant surfaces are not necessarily obtained using these processes. Heparin can be bound too tightly to the surface due to the high abundance of functional groups on the heparin, or coupling may result from bonds between the active pentasaccharide sequence on the heparin and the biomaterial, preventing activation of AT-III and thus catalytic deactivation of the proteases. In order to obtain truly anti-thrombogenic surfaces, proper immobilization of the biomolecules is key. Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generaton of thrombi and microemboli.

Besides the coupling of heparin via its natural functional groups or through a terminal aldehyde group, coupling of heparin via aldehyde groups randomly introduced into the chain by means of periodate oxidation has also been described. Solomon et al (in U.S. Pat. Nos. 4,600,652 and 4,642,242) and Hu et al (in U.S. Pat. Nos. 4,720,512; 4,786,556; 5,032,666 and 5,077,372) coupled heparin after periodate oxidation to an aminated polyurethane obtaining a material with high loading of stably bound heparin with the inventors claiming excellent antithrombogenicity for the material. However, no experimental data was presented to support their claim, The periodate oxidation of heparin was performed in a buffered aqueous solution of sodium periodate. The oxidation reaction was stopped by the addition of glycerol and the solution was then evaporated to dryness under nitrogen. For coupling, the dried heparin was reconstituted in an appropriate buffer. However, it has been noted that the amount of periodate used in the oxidaton reaction by Solomon et al and Hu et al can allow excessive oxidation of the heparin which would reduce its antithrombogenic properties. It has also been noted that the use of glycerol to stop the reaction can generate formaldehyde which can make coupling of the heparin more difficult. It has also been noted that drying the oxidized heparin is inconvenient and adds cost to the process.

It is therefore an object of the present invention to provide a biocompatible surface having active, covalently bonded biomolecules thereon.

It is also an object of the present invention to provide a method for oxidizing biomolecules having polysaccharide groups which allows for easy coupling of the biomolecule to an aminated substrate.

It is also an object of the present invention to provide an oxidized biomolecule which can be stored for later use in liquid form.

SUMMARY OF THE INVENTION

These and other objects are achieved by the present invention. We have discovered an improved method of making a medical device having immobilized heparin on a blood-contacting surface in which heparin is admixed with sufficient periodate to react with not more than two sugar units per heparin molecule in a buffer solution having a pH in the range of about 4.5–8. In particular, where sodium periodate is the periodate used, the weight ratio of heparin to the periodate is about 30:1 or less. This mixture is reacted for at least 3 hours while protected from light and is then applied to the immobilized amine groups without stopping the periodate-heparin reaction with glycerol. The application to the immobilized amine causes a reaction between the aldehyde groups on the heparin and the immobilized amine groups to form a Schiff base. A mild reducing agent like cyanoborohydride is used to stabilize the Schiff base into a secondary amine.

This is an improvement over the prior art method discussed above which included using an excess of periodate and then stopping the reaction at a desired point by the addition of glycerol since the conversion of only a few of the natural functional groups to aldehydes better preserves the antithrombotic bioeffectiveness of the heparin molecules bound to the surface. The invention also avoids the prior art steps of drying and reconstituting the heparin by providing a reacted mixture of heparin and periodate that can be stored as a stable liquid and applied directly to the mated surface several days later.

This method is particularly useful where the surface to bind to has a high amine density. For example, if the immobilized amine groups are provided by an immobilized coating of a polyalkyleneimine on the surface, there are so many potential binding sites on the polyalkyenelimine that it is unnecessary (and disadvantageous to the bioactivity of the surface) to have more than one or two reactive dialdehyde groups on the heparin molecules to be bound.

DETAILED DESCRIPTION OF THE INVENTION

In the present method, a medical device can be provided with a blood-compatible surface of improved biocompatibility. By medical device, is meant devices which have surfaces which contact blood in the course of their operation, which blood is subsequently used in the circulatory system of patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves and the like which are implanted in blood vessels or in the heart. This can also include devices for temporary intravascular use such as catheters, guide wires and the like which are placed into the blood vessels or the heart for purposes of monitoring or repair.

Improved antithrombotic surfaces are provided by the mobilization of heparin to the surface of the device by covalent bonding. By heparin, we mean glycosaminoglycans, a heterogenous group of straight-chain anionic mucopolysaccharides, having anticoagulant properties. The heparin used herein can be a preparation obtained from tissues in a manner conventional for the preparation of heparin as an anticoagulant. The heparin preparation can be obtained from a variety of mammalian tissues, including, if desired, human tissue. Generally, porcine or bovine sources are used with a preferred tissue for heparin starting material being porcine intestinal mucosa. Heparin preparations prepared from this tissue source are commercially available.

An essential aspect of the present invention is to provide the blood-contacting surface of the device with immobilized amine groups which are capable of bonding to aldehyde groups on the heparin molecule. Such amine groups can be provided by methods known to those skilled in the art. For example, amine-functional spacer molecules have been used to immobilize a biomolecule and/or biomolecules. The spacer insures that the active site of the biomolecule is held outward away from the support so as to contact the body fluid efficiently. The spacers are derived from organic molecules having at least two reactive functional groups, or more, generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radiofrequency plasma treatment by subjecting it to a radiofrequency electric field in the presence of a water vapor plasma medium. An aqueous solution of polyethyleneimine (PEI) and 1-(3-dimethylpropyl)-3-carbodiimide (EDC) coupling agent was applied to the radiofrequency plasma discharge modified polyurethane surface. An aqueous solution of heparin and EDC was then applied to the PEI-treated surface in order to provide a polymeric surface having an anti-thrombogenic agent seemed to its surface. However, considering the heterogeneity of the polyurethane surface even coating with the multi-functional spacer molecule is not guaranteed.

Additional coverage can be provided, for example, according to U.S. Pat. No. 4,565,740 to Golander et al. or U.S. Pat. No. 5,049,403 to Larm et al. In the first of these patents, a complex of a polymeric cationic surfactant (e.g. a polyalkyleneimine) and a dialdehyde (e.g. glutaraldehyde) is adsorbed onto a substrate material. In the second of these patents, a polyamine is adsorbed onto the surface of a substrate and crosslinked with crotonaldehyde. Multiple coatings, including intermediate layers of anionic material are then applied to obtain an effective coating. However, these crosslinked coatings rely on adsorption onto the surface and ionic bonding to the surface, which may not provide good bonding of the coating to the surface. The inventors of the present invention have contributed to improvements in biocompatibility of biomaterials through the use of multilayer coatings in their U.S. Pat. Nos. 5,229, 172; 5,308,641 and 5,350,800 which are incorporated herein by reference. For example, in U.S. Pat. No. 5,229,172, we discovered a method for modifying the surface characteristics of a polymeric material by providing a base layer of grafted acrylamide on the polymeric surface which can be used to attach various spacers and biomolecules. Or, in U.S. Pat. No. 5,308,641, we discovered an improved spacer material which includes a polyalkyeneimine covalently attached to an aminated substrate and crosslinked with a crosslinking agent which is difunctional in aldehyde groups. Or, in U.S. Pat. No. 5,350,800, we discovered a method for attaching a biomolecule having carboxyl groups to an aminated solid surface by a carbodiimide and then selectively restoring the bio-functionality of the carboxyl groups.

On metal or glass surfaces, the binding of the base layer of such multi-layer coatings can be a problem since there is no organic structure to provide covalent bonds between the metal or glass substrate and the grafted base layer. Others have addressed the problem of binding to metals and glass by applying aminosilanes to adhere to the surface and then attaching the biomolecule to the aminosilane through the amine functionality of the aminosilane. This can be seen in U.S. Pat. No. 5,355,433 issued to Rowland et al in which an aminosilane is used to adhere a heparin molecule to an oxidized tantalum surface. Aminosilanes are also disclosed for attachment of a heparin molecule to glass or metal surfaces in U.S. Pat. No. 4,118,485 issued to Eriksson et at.

Preferably, the immobilized amine functionality is provided in a manner similar to that disclosed in our U.S. Pat. No. 5,308,641 in which a polyalkyeneimine is covalently attached to a substrate.

By polyalkyleneimine, we mean to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkyleneimines employed in the present invention are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used in the present invention. The preferred molecular weight of such a polyethyleneimine could range from about 60,000 to about 1,000,000.

A critical aspect of the present invention is the controlled oxidation of the heparin molecules to provide a limited number of reactive aldehyde groups on the average heparin molecule. This is accomplished by adding a periodate to a buffered aqueous solution of the heparin and allowing it to react with the heparin. Any water soluble periodate can be used but preferably the periodate is an alkali metal periodate such as sodium periodate. The mount of periodate required is that sufficient to react with no more than two of the sugar units in the heparin molecule. By sugar, we mean the basic disaccharide residues constituting the structure of the glycosaminoglycan. If the periodate used is sodium periodate and the heparin used is a commercially available injectable form of heparin (i.e. its sodium salt with activity of 160 u/mg), the weight ratio of heparin to periodate should be about 30:1 or less in order to react with no more than two of the sugar units in the heparin molecule. It will be appreciated by those skilled in the art that the mount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to 8 can be used with lower pH (e.g. an acetate buffer at pH=4.5) being preferred if a rapid reaction is desired while a more neutral pH (e.g. a phosphate buffer at pH=6.88) is preferred for a slower reaction with a longer storage life. With the acetate buffer at a pH of 4.5, the reaction should proceed for about 3 hours while with a phosphate buffer at a pH of 6.88, the reaction should proceed for about 16 hours. If desired, the reacted solution may then be stored prior to use at about 5° C. The storage stability of the reacted mixture at a neutral pH can extend for 2 to 14 days.

Unlike the prior art compositions which required stopping the reaction with glycerol or glycol to eliminate excess periodate in the mixture and then drying the heparin, the reactive mixture of the present invention may be applied to the immobilized amine groups on the surface to be coated without the additional of a glycerol or glycol composition and without drying. Preferably, the reaction mixture is first diluted and the pH adjusted in order to bring the pH of the mixture to a pH which is favorable for the coupling reaction. For example, the reaction mixture can be diluted in an acetate buffer solution (pH=4.5). A mild reducing agent such as sodium cyanoborohydride is added to the diluted mixture to effect the reduction of the bonds formed between the reactive aldehyde groups on the oxidized heparin and the amine-functional groups immobilized on the surface to be treated. The surface to be treated is then immersed in the diluted mixture and incubated at a sufficient temperature and time to complete the reaction. For example, the reaction could be competed in about 1-3 hours at 50° C.

As an optional improvement, the surface having immobilized heparin thereon can be provided with an adsorbed protein molecule which is capable of inhibiting the action of thrombin to further prevent coagulation of fibrinogen. For example, antithrombin III which is known to be activated by heparin to inactivate thrombin.

The protein can be adsorbed onto the surface with immobilized heparin immediately before the device is brought into contact with a patient's blood (e.g. by the surgeon immediately before a medical device is implanted) or, the immobilized heparin with adsorbed protein can be provided in a sterile device by drying the device with the immobilized heparin and adsorbed protein thereon and then packaging and sterilizing the device by conventional means.

The following examples show how such a heparin coating can be provided on a metal surface.

EXAMPLE 1

A piece of coiled tantalum wire was ultrasonically cleaned in 2% Micro-clean for 30 minutes followed by ultrasonic treatment in deionized water for 30 minutes. This last step was repeated after which the coil was rinsed in isopropanol and dried at 50° C. for 20 minutes.

The cleaned coil was swirled in a 2% solution of trichlorovinylsilane (Merck Darmstadt, FRG) in xylene for 60 seconds followed by rinsing for 60 seconds in xylene, 60 seconds in isopropanol, 60 seconds in water and finally in acetone. The coil was then allowed to air dry overnight.

The dried coil was then placed into a glass robe which was filled with 15 ml of an aqueous solution of 35 wt % of fleshly distilled acrylic acid and 5 wt % acrylamide. To the 15 ml of monomer solution, 0.9 ml of a solution of ceric ammonium nitrate (0.1M) in nitric acid (0.1M) was added. Deaeration was performed for 3-5 minutes at about 18 mm Hg followed by ultrasonic treatment for 10 minutes and an additional incubation of 35–40 minutes, all at room temperature. The grafted samples were then rinsed 10 times with deionized water at 50° C. followed by an overnight incubation at 50° C. Samples taken showed a deep stain when soaked in toluidine blue solution.

A solution of 375 ml crotonaldehyde in 0.1M sodium borate (pH:=9.1) was made and after 10 minutes stirring polyethyleneimine (PEI, Polymin SN from BASF with a $M_w$ of 60,000) was added. After an additional mixing of 5 minutes, the coil was incubated in the crosslinked PEI solution for one hour while shaking. After rinsing with deionized water, the coil was contacted with a solution of 0.5 wt % PEI (Polymin SN) in 0.1M sodium borate (pH=9.1) for 10 minutes. Water soluble carbodiimide (1-(3-diethylaminopropyl)-3-ethylcarbodiimide. HCl) at a concentration of 0.05M was added. Coupling was allowed to proceed for one hour while shaking followed by rinsing with deionized water for 10 minutes.

Oxidized heparin was prepared by adding 0.165 mg $NaIO_4$/ml to 5 mg native heparin (Akzo)/ml 0.05M phosphate buffer (pH=6.88; 0.025M $K_2HPO_4$+$NaH_2PO_4 \cdot 2H_2O$). After overnight oxidation under the exclusion of light, the resulting heparin solution was diluted in 0.4M acetate pH=4.6 at a ratio of 1:20. 0.1 mg of $NaCNBH_3$/ml was added to the diluted heparin and the coil was incubated in this solution for 2 hours at 50° C. After rinsing with deionized water, 1M NaCl and water again to remove loosely bonded heparin, the coil was incubated with toluidine blue which provided an even lilac stain, indicating successful heparinization. An additional bioactivity test was also successfully performed to determine the ability of the heparinized surface to deactivate thrombin via activation of previously adsorbed antithrombin III. The bioactivity was also tested successfully after an overnight challenge with 1% sodium dodecylsulfate at 50° C. indicating excellent stability of the coating on the metal substrate.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for making a medical device having immobilized heparin on a blood-contacting surface comprising:
   (a) providing immobilized free amine groups on a blood-contacting surface;
   (b) admixing heparin with sufficient periodate to react with not more than two sugar units per heparin molecule in a buffer solution having a pH in the range of about 4.5–8, and allowing the admixture to react for at least 3 hours while protected from light; and
   (c) applying the reacted admixture to the immobilized amine groups without stopping the periodate-heparin reaction.

2. The method of claim 1 wherein the mobilized amine groups are provided by an immobilized coating of a polyalkyleneimine.

3. The method of claim 1 wherein the reacted admixture is stored for 2 to 14 days prior to application to the immobilized amine groups.

4. The method of claim 1 wherein the periodate is sodium periodate.

5. The method of claim 4 wherein the weight ratio of heparin to periodate is about 30:1 or less.

6. The method of claim 1 further comprising mixing the reacted admixture with a mild reducing agent prior to applying to the immobilized amine groups.

7. The method of claim 6 wherein the reducing agent is sodium cyanoborohydride.

8. The method of claim 7 wherein the pH of the reducing agent and reacted admixture is adjusted to about 4.6.

9. A method for applying a heparin coating to a surface comprising:
   (a) attaching a polyalkyleneimine to the surface;
   (b) preparing a heparin solution by the steps comprising:
      (1) admixing heparin with a periodate in a buffered aqueous solution at a weight ratio of heparin to periodate of about 30:1;
      (2) reacting the admixture for at least 3 hours while protected from light; and
      (3) adding a cyanoborohydride to the reacted admixture;
   (c) applying the heparin solution to the attached polyalkyleneimine on the surface;
   (d) incubating the surface and applied heparin such that the heparin and the polyalkyleneimine are bonded; and
   (e) rinsing the incubated surface with water.

10. The method of claim 9 wherein the polyalkyleneimine is attached to the surface by applying a silane to the surface and covalently bonding the polyalkyleneimine to the silane.

* * * * *